United States Patent [19]

Smith

[11] 4,005,706
[45] Feb. 1, 1977

[54] TYPE OF ADHESIVE CEMENT AND CERTAIN IMPROVED PRODUCTS MADE POSSIBLE THEREBY

[76] Inventor: David F. Smith, 6511-1 Bay Club Drive, Fort Lauderdale, Fla. 33308

[22] Filed: June 9, 1975

[21] Appl. No.: 585,382

Related U.S. Application Data

[63] Continuation-in-part of Ser. No. 473,751, May 28, 1974, abandoned.

[52] U.S. Cl. .............................. 128/90; 260/998.11
[51] Int. Cl.² ........................................ A61L 15/07
[58] Field of Search ............... 128/90, 89, 155–156; 428/343; 260/998.11, 42.73, 42.51; 96/1.8

[56] References Cited

UNITED STATES PATENTS

| | | | |
|---|---|---|---|
| 2,904,526 | 9/1959 | Uelzmann | 96/1.8 |
| 3,607,262 | 9/1971 | Ueda et al. | 96/1.8 |
| 3,708,290 | 1/1973 | Verhille et al. | 96/1.8 |
| 3,751,391 | 8/1973 | Smith | 260/998.11 |
| 3,776,724 | 12/1973 | Usmani | 96/1.8 |

FOREIGN PATENTS OR APPLICATIONS

| | | |
|---|---|---|
| 1,139,430 | 1/1969 | United Kingdom |
| 1,316,129 | 5/1973 | United Kingdom |

*Primary Examiner*—G.E. McNeill

[57] ABSTRACT

New types of fast setting zinc oxide-polycarboxylic acid adhesive cements are disclosed as well as certain improved products the use of these cements makes possible.

Certain new types of cement have been disclosed by Dennis Clifford Smith (British Pat. No. 1,139,430, Jan. 8, 1969) and by Alan Donald Wilson and Brian Ernest Kent (British Pat. No. 1,316,129, May 9, 1973). These cements were designed for dental use. The former involves the reaction of ZnO with 40–60% aqueous polyacrylic acid of molecular-weight 15000–150000. (I have discovered that polymethacrylic acid is substantially the equivalent of polyacrylic acid in these cements.) The polyacrylic acid solution is relatively expensive. The latter cement involves a high temperature fusion as well as the polyacrylic acid. While these products are undoubtedly excellent for dental use and such use can tolerate their high cost, certain of my uses require a much cheaper product and also a dry, powdery solid acid that is quick to dissolve. It is difficult and expensive to produce such a form of polyacrylic acid. I have discovered very effective adhesive cements that are much cheaper, more readily available in a form convenient to use and controllably settable. My adhesive cement is also more adhesive shortly after wetting and avoids the possibility of skin reaction with use of polyacrylic acid due to the presence of some acrylic acid of a low degree of polymerization especially where large areas of skin are contacted and where the user is subject to repeated contact with the cement.

10 Claims, No Drawings

TYPE OF ADHESIVE CEMENT AND CERTAIN IMPROVED PRODUCTS MADE POSSIBLE THEREBY

This application is a continuation-in-part of my co-pending application Ser. No. 473,751, filed May 28, 1974 now abandoned.

The following examples are illustrative but not limiting of my invention.

EXAMPLE 1

345 grams anhydrous citric acid and 260 grams ZnO were thoroughly mixed with 460 ml. isopropyl alcohol. While actively stirring this slurry, there was added as binder a solution of 14 g. polyvinyl acetate (softening or heat-sealing temperature 230°–240° f.) in 160 ml. methylene chloride. This slurry was spread on 32×28 mesh surgical gauze and passed through a drying oven at 230° F. to yield a dry, discontinuously coated gauze weighing about 210 g. per 4 inch by 5 yd. bandage roll. The coated gauze may weigh from 70 to 250 g. per roll. The gauze alone weighs about 18 g. The product was wet in water and the excess water squeezed out with very little loss of coating. The bandage warmed up almost immediately, became highly adhesive and very shortly took a hard set. The set material was still hard after standing in water for 4 days. The ZnO was very fine, 99.7% through 325 mesh screen and, of course, relatively insoluble in water. The citric acid was very soluble in water, 133 g. per 100 g. $H_2O$. The 375 g. citric used is equivalent to 209.7 g. ZnO, leaving 50 g. excess ZnO. I may use up to 300 % excess ZnO if I wish to reduce the temperature rise thereby, but preferably I use 10–25% in order to assure water resistance.

EXAMPLE 2

The experiment of Example 1 was repeated using 369 g. citric acid and 235 g. ZnO, and as binding agent 7 g. of the polyvinyl acetate dissolved in 160 ml. methyl cellosolve. The weight of coating was about 1/3 that of Example 1. When the product was wet in water and excess water squeezed out of the bandage roll, there was much less temperature rise and, although the final set was very hard, the set time was considerably longer than in Ex. 1. When soaked in water, the cast softened slightly. In this case the citric and ZnO were chemically equivalent.

EXAMPLE 3

The experiment of Ex. 2 was repeated except that 454 g. citric acid and 151.2 g. ZnO were used. Results were similar to those of Ex. 2 but when soaked in water, the cast softened considerably. In this experiment there was excess citric acid.

EXAMPLE 4

Aged (and brittle) carboxylated cellulose, malonic acid, malic acid and maleic acid each was separately reacted with ZnO to produce adhesive material followed by formation of hard cement in a way similar to that with citric acid. One sample of tartaric acid, however, did not yield a "stringy" adhesive mass like with citric acid but it was found that this sample of tartaric acid was somewhat slow to wet in spite of being very soluble. In general it appears that polycarboxylic acids that are readily (quickly) soluble, considerably soluble and quickly wet show reaction with ZnO as does citric acid.

EXAMPLE 5.

A portion of the ZnO of Ex. 1 was heated for several hours at 1000°–1100° C. and then mixed in the proportion of 375 g. dry, anhydrous citric acid and 260 g. of the ZnO. A small portion of this mixture was placed on one side of a glass plate and 6 drops (0.3 g.) water placed on another portion of the plate. Enough powder was mixed into the water with a spatula (as done in dental practice) to yield a thick paste whose set was delayed for about 8 minutes. This paste can be used as a so-called "surgical cement" by dentists as a temporary dental filling, a cavity liner, etc. or in orthopedics to assist in resetting of fractured bone material.

Control of the rate of reaction of ZnO is as above by heating or by dilution up to about 300% of the weight of the mix with finely-divided MgO, $Bi_2O_3$, $Ca_3(PO_4)_2$ or $Ca F_2$ in the case of dental or surgical use or, in the case of orthopedic bandages (Ex.1), by use of coatings down to 70 g. per sq.ft., or by dilution with such finely divided solids as silica, clay, diatomaceous earth, etc., or by use of excess ZnO. The dilution is, of course, at some sacrifice of strength in the final cement. The set can also be slowed by using a larger proportion of water. While the particle size of the acid is not of great importance so long as it quickly wets and dissolves, it should be at least as fine as about 100 mesh. Increase of particle size of the ZnO, however, will effectively slow the set. A ½ hour heating at 800° to 900° C. is reported to decrease its rate of reaction with acid about 4-fold. This procedure is available from the manufacturer at a nominal cost. Some commercial ZnO is coated to the extent of about 0.5% by weight with propionic or lauric acid which forms the corresponding zinc salt by reaction on the surface of the ZnO, or the ZnO may be coated with other hydrophobic material like mineral oil which slows the wetting of the ZnO by water. The soluble acid should not have an ionization constant above about $10^{-3}$ for the first hydrogen in order not to be irritating on the skin for dental and surgical use and for such use, of course, should not be toxic or allergenic to most individuals.

ZnO is normally produced by air oxidation of pure Zn vapor (French process) or roasting of Zn ore with coal and subsequent oxidation (American process). In either case, the particle size is normally very small, 99–99.97% through 325 mesh and the % ZnO is 99.2–99.8. As indicated, however, some ZnO as received from the manufacturer has about 0.5% of the hydrophobic coating. ZnO may also be made by heating $ZnCO_3$ or I may use $ZnCO_3$ in place of ZnO in my adhesive cement. For surgical and dental use, U.S.P. XIII ZnO may be used although the commercial grade is very pure.

The examples show that cements using excess soluble acid over the chemical equivalent of the ZnO (Ex. 3), while yielding a highly adhesive product, are not water resistant as are those using equivalent amounts of ZnO and acid (Ex. 2) and the most highly water resistant are those using an excess of ZnO over acid (Ex. 1). In an orthopedic bandage, a water insoluble bonding agent can be used as in Examples 1–3. However in such a product, unless used to slow the wetting of the ZnO, the mix should not be completely covered with a binder that is neither soluble nor water wettable. Water insoluble but water wettable binders are (1) dextran which can be used in solution in anhydrous methanol, ethanol, propanol or isopropanol as slurry solvent (2) Zein dissolved in a mixture of methylene chloride and methanol. Bonding agents that can be used to slow the wetting are (1) solutions of polyvinyl acetate in toluene, methyl cellosolve or methylene chloride (2) ethyl cellulose and other water insoluble, inert materials in anhydrous solution (3) copolymers of vinyl acetate and acrylate or methacrylate esters in solvents such as toluene or methylene chloride (4) solutions of shellac, silicones or cellulose acetate in anhydrous solvents. However, such binders must be applied so as not to form continuous coatings i.e. they must be applied as finely divided dispersions of the solid materials so as to leave at least some areas uncovered.

In the ways described the set may be slowed as desired. Slowing the set also limits the temperature rise. When covering a considerable area of the human body with the bandage described, one does not want the temperature to exceed about 140° F. This is achieved by slowing the set as described, using excess water, diluting with inert materials as described, using excess reactants or by combinations of these devices.

In order to further strenghten and waterproof my cement, I may add an uncured melamine-formaldehyde resin with a mol ratio of melamine to formaldehyde from about 1:1:.5 to 1:3.3 and preferably from 1:1.7 to 1:2.5, respectively; in amount from 5 to 30% by weight based on solids in the adhesive, preferably 10 to 20%. An acid reacting resin condensation catalyst is also included in amount from 1 to 10% of the weight of resin and comprising one or more of the following: ammonium chloride, a mixture of equivalent amounts of ammonium sulfate and potassium chloride, stannous chloride dihydrate and aluminum chloride hexahydrate. Any of the anhydrous slurry liquids disclosed may be used, following the procedures of U.S. Pat. No. 2,842,120. When using such resin, I also prefer to use polyvinyl pyrrolidone of molecular-weight 10,000 to 360,000 in amount from 10 to 150% of the weight of resin, as in U.S. Pat. No. 3,671,280,with a preference for 50 to 100%. The resin condensation catalyst may be omitted from the slurry and applied in solution or suspension, for example, with or without water soluble polyethylene glycol of melting-point slightly above room temperature, in anhydrous methanol or methanol and methylene chloride, to the dried bandage when the adhesive cement is used to produce bandage.

It should be added that, in the case of the orthopedic bandage, the use of a bonding agent to bond the particles of the spread to themselves and to the backing, such an agent is not necessarily used but when used is in amount from 0.5 to 1.5 per cent of the weight of the spread.

The properties hereinbefore cited as required of those polycarboxylic acids I find useful, will distinguish them from among the possible polycarboxylic acids— which are extremely numerous, for example, when one considers the various halogen substitution products of even the more than 20 simple dibasic acids let alone the polyhalogen and mixed halogen plus the alkyl and aryl group substitution products of the higher polycarboxylic acids and the numerous permutations of and with the various possible substituents.

While in so called surgical cements, up to about 10 per cent of the weight of the zinc oxide may be replaced by MgO, $Bi_2O_3$, $Ca_3(PO_4)_2$ or $CaF_2$, I prefer to use ZnO alone.

Having thus described my invention, what I claim is:

1. An orthopedic bandage comprising a thin, porous, flexible, inert backing material carrying a substantially uniform discontinuous spread of an intimate mixture of a dry, finely-divided zinc oxide and a dry, finely-divided, essentially non-allergenic, non-toxic, rapidly water-wettable and very water-soluble, weak polycarboxylic acid, the proportion of zinc oxide to acid being from that which is chemically equivalent to the acid up to 300 per cent in excess of its equivalent, the amount of the spread being from 70 to 250 grams per 5 square feet of backing, said mixture being such as to become rapidly adhesive when wet with water at room temperature and shortly thereafter to set forming a strong, firm mass.

2. The bandage of claim 1 wherein the said zinc oxide has been inactivated by heating.

3. The bandage of claim 1 wherein the said acid is citric acid.

4. The bandage of claim 1 wherein the said spread contains from 0.5 to 1.5 per cent of its weight of a water-insoluble, non-water-wettable bonding agent with heat-sealing temperature from about 230° to 240° F., in the form of a fine dispersion and selected from at least one of the class consisting of polyvinyl acetate, ethyl cellulose, shellac, silicones, cellulose esters and copolymers of vinyl acetate, acrylate and methacrylate esters.

5. The bandage of claim 1 wherein the said spread contains from 0.5 to 1.5 per cent of its weight of a water-insoluble, water-wetable bonding agent uniformly distributed throughout the spread and selected from the class consisting of dextran and zein.

6. The bandage of claim 1 wherein the set is delayed by dilution of said spread with up to about 300 per cent of the weight of said spread with at least one material selected from the class consisting of finely-divided MgO, $Bi_2O_3$, $Ca_3(PO_4)_2$, $CaF_2$, silica, clay, diatomaceous earth and excess ZnO.

7. The bandage of claim 1 wherein the said zinc oxide is replaced by zinc carbonate.

8. The bandage of claim 1 wherein the said spread additionally contains from 5 to 20per cent of its weight of a dry, uncured melamine-formaldehyde resin with a mol ratio of melamine to formaldehyde from about 1:1.5 to 1:3.3, dry polyvinylpyrrolidone of molecular-weight between 10,000 and 360,000 in amount from 10 to 150 per cent of the weight of resin and at least one dry resin-condensation catalyst selected from the class consisting of ammonium chloride, equivalent amounts of ammonium sulfate and potassium chloride, stannous chloride dihydrate and aluminum chloride hexahydrate.

9. The bandage of claim 1 wherein the said zinc oxide has a thin, uniform coating of an inert, water-insoluble, hydrophobic material in amount up to about 0.5 per cent of its weight.

10. The bandage of claim 1 wherein up to about 10 per cent of the weight of the said zinc oxide is replaced by a material selected from the class consisting of MgO, $Bi_2O_3$, $Ca_3(PO_4)_2$ and $CaF_2$.

* * * * *